United States Patent
Tracy et al.

(10) Patent No.: US 10,988,784 B2
(45) Date of Patent: Apr. 27, 2021

(54) METHOD FOR PRODUCING A BIOPRODUCT SELECTED FROM ACETONE, ISOPROPANOL AND COMBINATIONS THEREOF

(71) Applicant: White Dog Labs, Inc., New Castle, DE (US)

(72) Inventors: Bryan Patrick Tracy, Wilmington, DE (US); Shawn William Jones, Bear, DE (US); Daniel Knox Mitchell, Wilmington, DE (US); Aharon M. Eyal, Jerusalem (IL); Karthikeyan Ramachandriya, Melrose, MA (US)

(73) Assignee: WHITE DOG LABS, INC., New Castle, DE (US)

( * ) Notice: Subject to any disclaimer, the term of this patent is extended or adjusted under 35 U.S.C. 154(b) by 331 days.

(21) Appl. No.: 15/765,391

(22) PCT Filed: Sep. 30, 2016

(86) PCT No.: PCT/US2016/054765
§ 371 (c)(1),
(2) Date: Apr. 2, 2018

(87) PCT Pub. No.: WO2017/059244
PCT Pub. Date: Apr. 6, 2017

(65) Prior Publication Data
US 2018/0305720 A1 Oct. 25, 2018

Related U.S. Application Data

(60) Provisional application No. 62/236,189, filed on Oct. 2, 2015.

(51) Int. Cl.
| | |
|---|---|
| *C12P 7/04* | (2006.01) |
| *C12P 7/10* | (2006.01) |
| *C12P 7/28* | (2006.01) |
| *C12P 7/20* | (2006.01) |
| *C12P 7/30* | (2006.01) |
| *C12P 7/54* | (2006.01) |
| *C12P 13/04* | (2006.01) |
| *B01D 61/14* | (2006.01) |
| *C12N 9/10* | (2006.01) |

(52) U.S. Cl.
CPC .................. *C12P 7/30* (2013.01); *C12P 7/04* (2013.01); *C12P 7/28* (2013.01); *C12P 7/54* (2013.01); *C12P 13/04* (2013.01); *B01D 61/14* (2013.01); *B01D 2311/25* (2013.01); *C12N 9/1029* (2013.01); *Y02P 20/582* (2015.11)

(58) Field of Classification Search
CPC ..... C12P 7/64; C12P 7/16; C12N 1/20; C07C 51/48; C07C 51/80; C07C 51/86; C07C 51/58
See application file for complete search history.

(56) References Cited

U.S. PATENT DOCUMENTS

| | | | |
|---|---|---|---|
| 8,993,289 B1 | 3/2015 | Wright | |
| 2010/0304453 A1 | 12/2010 | Trawick et al. | |
| 2010/0330633 A1 | 12/2010 | Walther et al. | |
| 2013/0052702 A1* | 2/2013 | Saunders | ............... C07K 14/37 435/134 |
| 2014/0311889 A1 | 10/2014 | Zaher et al. | |
| 2016/0251683 A1 | 9/2016 | Tracy et al. | |

FOREIGN PATENT DOCUMENTS

WO    2015/134246 A1    9/2015

OTHER PUBLICATIONS

Fast et al., "Acetogenic mixotrophy: novel options for yield improvement in biofuels and biochemicals production.", *Current Opinion in Biotechnology* 33:60-72 (2015).
International Search Report issued in PCT/US2016/054765, dated Dec. 29, 2016.
International Preliminary Report on Patentability issued in PCT/US2016/054765, dated Apr. 3, 2018.
U.S. Appl. No. 62/236,189, filed Oct. 2, 2015.
Supplementary European Search Report in EP Application No. 16852708, dated May 23, 2019.
Tashiro et al., "High production of acetone-butanol-ethanol with high cell density culture by cell-recycling and bleeding," *Journal of Biotechnology*, 2005, 120:197-206.
Jones et al., "CO2 fixation by anaerobic non-photosynthetic mixotrophy for improved carbon conversion," *Nature Communications*, 2016, Sep. 30, 2016, 1-9.

* cited by examiner

*Primary Examiner* — Maryam Monshipouri
(74) *Attorney, Agent, or Firm* — Greenblum & Bernstein, P.L.C.

(57) ABSTRACT

Methods for producing a bioproduct selected from acetone, isopropanol and a combination thereof with a microorganism in a fermentor are disclosed. The methods include separating cells of the microorganism from a fermentation broth to form separated cells and recycling at least a fraction of the separated cells to the fermentor to achieve one or more of the following: (1) cell concentration in said fermentor greater than 2 g/L; mass yield on a first feedstock greater than 32%; productivity greater than 0.12 g/L/h; and bioproduct titer greater than 10 g/L.

18 Claims, 7 Drawing Sheets
Specification includes a Sequence Listing.

METHOD FOR PRODUCING A BIOPRODUCT SELECTED FROM ACETONE, ISOPROPANOL AND COMBINATIONS THEREOF

CROSS REFERENCE TO RELATED APPLICATIONS

The instant application claims priority to U.S. Provisional Application No. 62/236,189, filed Oct. 2, 2015, the disclosure of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Jun. 22, 2018, is named P54658_SL.txt and is 11,214 bytes in size.

FIELD OF THE INVENTION

The invention relates to the field of production of bioproducts such as acetone and isopropanol with microorganisms.

BACKGROUND

Acetone is a clear, colorless, volatile liquid with a sweet odor. It is the simplest aliphatic ketone and the most commercially important. Nearly all world production of acetone is via cumene peroxidation, as a coproduct with phenol. Its main use is as a chemical intermediate in the manufacture of acetone cyanohydrin for use in the production of MMA, bisphenol A and aldol chemicals. Direct solvent applications also account for a large portion of world demand. Global market size of acetone is estimated at over 5.9 million tons in 2014, valued at over $7 billion. Consumption growth is projected at a 3% compound annual growth rate (CAGR), and our experience suggests there is considerable interest to switch to renewable acetone suppliers.

Isopropanol (IPA) is also a clear, colorless, volatile alcohol with a sweet odor. It is a three carbon, secondary alcohol with a variety of industrial uses such as a direct solvent and as a feedstock for the production and processing of acrylics, epoxy resins, ethyl cellulose, natural resins, gums, polyvinyl butyral, alkaloids and some essential oils. Global market size of IPA is estimated at over 2.1 million tons, valued at over $2.8 billion. Consumption growth is projected at a 6.9% CAGR, and our experience again suggests there is considerable interest to switch to renewable IPA suppliers.

Although it has been demonstrated that acetone and IPA could be derived from renewable feedstocks via fermentation, the theoretical best mass yield on glucose is 32.2 wt % and 33.3 wt % for acetone and IPA respectively, and neither maximum has ever been demonstrated to our knowledge. This low mass yield is not sufficient to justify producing either acetone or IPA from sugar feedstocks via fermentation, as sugar input cost is too high to render an economically viable process when compared to the petrochemical production processes. Meantime, we have invented and disclosed fermentation organisms and processes that theoretically can produce acetone and IPA at 48.3 wt % and 50 wt % mass yields, respectively. However, all microorganisms do need to consume a portion of the sugar to generate themselves, and IPA requires more reducing power than is available in sugar under more realistic fermentation conditions, therefore more accurate theoretical maximum mass yields for acetone and IPA are 46 wt % and 44 wt %, respectively. Furthermore, we have demonstrated the production of acetone and IPA at 44 wt % and 41 wt % fructose conversion, respectively. We accomplish these high mass yields through a process we called mixotrophic fermentation, which we have thoroughly described and reviewed elsewhere (Fast, A G, Schmidt, E D, Jones, S W, & Tracy, B T. 2015. "Acetogenic mixotrophy: novel options for yield improvement in biofuels and biochemical production." *Curr Opin Biotechnol* 33:60-72). Through mixotrophy, our organisms simultaneously consume sugar and fix $CO_2$ and $H_2$. In one specific embodiment, they consume a portion of the $CO_2$ and $H_2$ evolved during glycolysis into acetyl-CoA, which is converted by the organism to acetone and/or IPA. The result is less $CO_2$ and $H_2$ evolved during glycolysis, and higher sugar to biochemical product yields as we previously mentioned. Accordingly, we have been able to overcome the challenges of low feedstock conversion to desired product of interest. However, there is an additional challenge for acetone and IPA fermentation, which is productivity. Industrial fermentations are commonly operated in a batch mode, whereby media is introduced into a bioreactor, the media is inoculated with a growing organism, fermentation proceeds till all substrate is consumed, and the fermenter is evacuated. Unfortunately the organism cell mass only accumulates to <5 g/L cell dry weight in a batch process, which results in very low productivities of <0.1 g/L/hr. In order to increase productivities, cell mass must be concentrated while maintaining mixotrophic acetone and IPA production and while maintaining a sufficiently low acetone and IPA concentration such that the organism is not inhibited.

SUMMARY OF THE INVENTION

Provided herein is a method for producing a bioproduct selected from acetone, isopropanol and a combination thereof, comprising (i) providing a first feedstock, a nitrogen source and optionally a second feedstock to form a fermentation medium; (ii) providing an isolated organism capable of metabolizing $CO_2$ into acetyl-CoA; (iii) culturing said organism in a fermentor in said fermentation medium whereby said first feedstock and optionally said second feedstock are metabolized and a fermentation broth is formed, which broth comprises said bioproduct; (iv) separating cells from said fermentation broth to form separated cells; (v) recycling at least a fraction of said separated cells to the fermentor; and (vi) separating said bioproduct to form separated bioproduct; which producing is characterized by one or more of the following criteria (a) cell concentration in said fermentor being greater than 2 g/L; (b) mass yield on first feedstock being greater than 32%; (c) productivity being greater than 0.12 g/L/h; and (d) total bioproduct titer being greater than 10 g/L.

According to an embodiment, said bioproduct is acetone.

According to an embodiment, said bioproduct is isopropanol.

According to an embodiment, said method is characterized by at least two of said criteria.

According to an embodiment, said method is characterized by at least three of said criteria.

According to an embodiment, said method is characterized by said four criteria.

According to an embodiment, said organism is selected from the group consisting of *Clostridium ljungdahlii*, *Clostridium autoethanogenum*, *Clostridium ragsdalei*,

*Eubacterium limosum, Butyribacterium methylotrophicum, Moorella thermoacetica, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia products, Clostridium glycolicum, Clostridium magnum, Clostridium mayombei, Clostridium methoxybenzovorans, Oxobacter pfennigii, Thermoanaerobacter kivui, Sporomusa ovata, Thermoacetogenium phaeum, Acetobacterium carbinolicum, Sporomusa termitida, Moorella glycerini, Eubacterium aggregans, Treponema azotonutricium*, and *Terrisporobacter glycolicus*.

According to an embodiment, said first feedstock comprises carbohydrates, glycerol, methanol, or combinations thereof.

According to an embodiment, said nitrogen source is selected from the group consisting of ammonium salts, urea, yeast extract, molasses, corn water-insolubles, corn steep liquor, ethanol stillage or combinations thereof.

According to an embodiment, said first feedstock comprises a carbohydrate.

According to an embodiment, said second feedstock comprises CO, $CO_2$, carbonate, bicarbonate, $H_2$, glycerol, methanol, formate, urea or mixtures thereof.

According to an embodiment, said providing a first feedstock comprises fractionating corn and said fermentation broth comprises at least 10 g/L of corn water-insoluble matter.

According to an embodiment, said separating cells comprises filtering the fermentation broth to obtain a retentate and a permeate and recycling at least a fraction of said retentate to the fermentor.

According to an embodiment, said fermentation broth comprises corn water-insoluble matter and said retentate comprises cells and corn water-insoluble matter at cell to insoluble matter weight/weight ratio in a range between 10:1 and 1:10.

According to an embodiment, said separating bioproduct comprises evaporating to form a vapor phase comprising said bioproduct.

According to an embodiment, said vapor phase further comprises $CO_2$ and said method further comprises separating at least a fraction of the $CO_2$ from bioproduct and recycling said at least a fraction of said separated $CO_2$ to said fermentor.

According to an embodiment, said fermentation broth further comprises at least one fermentation co-product and the weight/weight ratio between said co-product and said bioproduct is in range between 0.01 and 1.

According to an embodiment, said filtering comprises microfiltration.

According to an embodiment, at least a portion of said bioproduct is separated from said permeate.

According to an embodiment, said bioproduct is acetone and the method further comprises catalytically converting said separated acetone into at least one acetone derivative. According to an embodiment, said acetone derivative is selected from mesitylene (1-3-5-trimethylbenzene), isophthalic acid, uvitic acid, meta-xylene and combinations thereof.

According to an embodiment, said evaporating is conducted at a temperature in the range between 30° C. and 90° C. According to an embodiment, said evaporating is conducted at a pressure in the range between 0.1 bar and 1 bar.

According to an embodiment, said evaporating forms bioproduct-depleted thin stillage, providing a first feedstock comprises fractionating corn, and said method further comprises adding said thin stillage to said fractionating corn to form a first feedstock comprising both fractionating corn and thin stillage.

According to an embodiment, said evaporating forms bioproduct-depleted thin stillage, and providing a first feedstock comprises diluting, said diluting being achieved in whole or in part with said thin stillage.

According to an embodiment, said evaporating forms bioproduct-depleted thin stillage, said thin stillage comprises an organic acid, and the method further comprises recycling said organic acid to said fermentor, wherein said organic acid is metabolized.

According to an embodiment, said organic acid comprises acetic acid.

According to an embodiment, said evaporating forms bioproduct-depleted thin stillage and the method further comprises drying said thin stillage to form a thick stillage and evaporated process water, which evaporated process water comprises a fermentation co-product.

According to an embodiment, said providing a first feedstock comprises fractionating corn, and the evaporated process water is recycled for use in said fractionating.

According to an embodiment, said providing a first feedstock comprises diluting, the diluting being achieved in whole or in part with said evaporated process water.

According to an embodiment, said co-product is an organic acid and the method further comprises recycling said organic acid to said fermentor, wherein said organic acid is metabolized.

According to an embodiment, said organic acid comprises acetic acid.

According to an embodiment, said providing a first feedstock comprises fractionating corn, said first feedstock comprises at least one corn-derived compound and said corn-derived compound provides at least a fraction of said nitrogen source. According to an embodiment, said corn-derived compound comprises at least one amino acid.

DEFINITIONS

Figure 1:
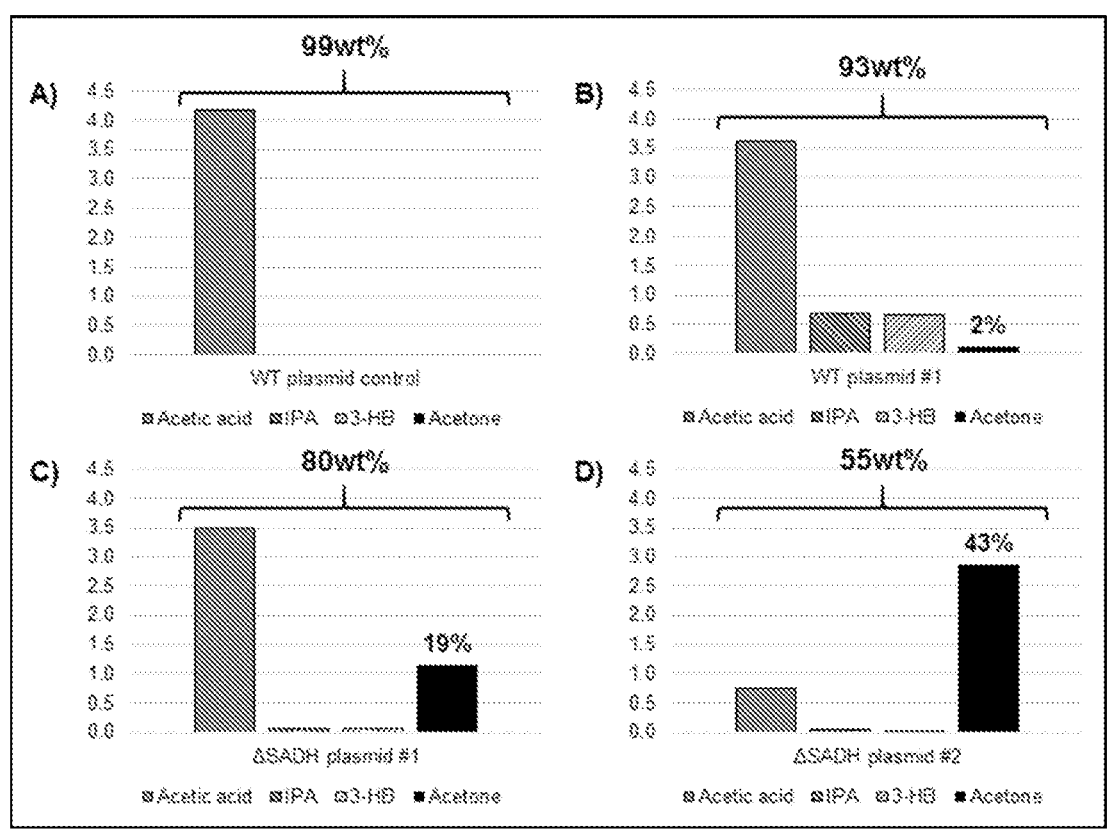
FIG. 1. Enhanced mass yields of acetone with mixotrophy. Metabolite analysis of four *C. ljungdahlii* strains after 7 days. Metabolites that were produced are acetic acid, isopropanol (IPA), 3-hydroxybutyric acid (3-HB), and acetone. Mass yields of acetone are indicated above its bar graph and the total mass yields of all products is indicated above all metabolites. Panel A is the wild-type (WT) strain with a plasmid control, panel B is the WT strain with an acetone pathway plasmid (plasmid #1), panel C is a SADH deletion strain (ΔSADH) with plasmid #1, and panel D is the ΔSADH strain with a second acetone pathway plasmid (plasmid #2). The y axis in all panels is titer (g/1).

As used herein, the term "bioproduct" refers to a fermentation product of interest, typically to the fermentation product of highest concentration in a fermentation broth.

As used herein, the term "feedstock" refers to at least one carbon source for fermentation.

As used herein, the terms "cell" and "cells" refer to the metabolizing organism.

As used herein, the term "mass yield on first feedstock" refers to the weight/weight ratio between bioproduct formed in said fermentation broth and in said provided first feedstock presented in %, i.e. weight of bioproduct formed in said fermentation broth/[weight of the provided first feedstock]×100.

As used herein, the term "corn water-insoluble matter" refers to water-insoluble matter resulting from corn treatment, e.g. from corn fractionation.

As used herein, the term "productivity" refers to the total amount of bioproduct produced per hour.

Unless specified otherwise, all ratios are weight per weight (weight/weight) ratios and all percents are weight percents.

DETAILED DESCRIPTION OF THE INVENTION

Provided herein is a method for producing a bioproduct selected from acetone, isopropanol and a combination thereof, comprising (i) providing a first feedstock, a nitrogen source and optionally a second feedstock, to form a fermentation medium; (ii) providing an isolated organism capable of metabolizing $CO_2$ into acetyl-CoA; (iii) culturing said organism in a fermentor in said fermentation medium whereby said first feedstock and optionally said second feedstock are metabolized and a fermentation broth is formed, which broth comprises said bioproduct; (iv) separating cells from said fermentation broth to form separated cells; (v) recycling at least a fraction of said separated cells to the fermentor; and (vi) separating said bioproduct to form separated bioproduct; which producing is characterized by one or more of the following criteria (a) cell mass concentration in said fermentor being greater than 2 g/L; (b) mass yield on first feedstock being greater than 32%; (c) productivity being greater than 0.12 g/L/h; and (d) bioproduct titer being greater than 10 g/L.

According to an embodiment, said bioproduct is acetone. According to an embodiment, said bioproduct is isopropanol.

According to an embodiment, said cell mass concentration in said fermentor is greater than 2 g/L, greater than 6 g/L, greater than 9 g/L or greater than 15 g/L. According to an embodiment, said mass yield on first feedstock is greater than 32%, greater than 35%, greater than 38%, greater than 41%, greater than 44%, greater than 47%% greater than 50%, greater than 52%, greater than 54% or greater than 55%. According to an embodiment, said productivity is greater than 0.1 g/L/h, greater than 0.5 g/L/h, greater than 1 g/L/h, greater than 1.5 g/L/h, greater than 2 g/L/h, greater than 2.5 g/L/h or greater than 3 g/L/h. According to an embodiment, said bioproduct titer is greater than 5 g/L, greater than 10 g/L, greater than 20 g/L or greater than 40 g/L.

According to an embodiment, said method is characterized by at least two of said criteria. According to an embodiment, said method is characterized by cell concentration in said fermentor being greater than 2 g/L and productivity being greater than 0.12 g/L/h. According to an embodiment, said method is characterized by mass yield on first feedstock being greater than 32% and productivity being greater than 0.12 g/L/h. According to an embodiment, said method is characterized by cell concentration in said fermentor being greater than 2 g/L and mass yield on first feedstock being greater than 32%. According to an embodiment, said method is characterized by cell concentration in said fermentor being greater than 2 g/L and bioproduct titer being greater than 10 g/L. According to an embodiment, said method is characterized by mass yield on first feedstock being greater than 32% and bioproduct titer being greater than 10 g/L. According to an embodiment, said method is characterized by productivity being greater than 0.12 g/L/h and bioproduct titer being greater than 10 g/L.

According to an embodiment, said method is characterized by at least three of said criteria. According to an embodiment, said method is characterized by cell concentration in said fermentor being greater than 2 g/L, mass yield on first feedstock being greater than 32% and productivity being greater than 0.12 g/L/h. According to an embodiment, said method is characterized by cell concentration in said fermentor being greater than 2 g/L, mass yield on first feedstock being greater than 32%, and bioproduct titer being greater than 10 g/L. According to an embodiment, said method is characterized by cell concentration in said fermentor being greater than 2 g/L, productivity being greater than 0.12 g/L/h, and bioproduct titer being greater than 10 g/L.

According to an embodiment, said method is characterized by cell concentration in said fermentor being greater than 2 g/L, mass yield on first feedstock being greater than 32%, productivity being greater than 0.12 g/L/h and bioproduct titer being greater than 10 g/L.

According to an embodiment, said provided first feedstock comprises carbohydrates, glycerol, methanol, and nitrogen source or combinations thereof. According to an embodiment, said first feedstock comprises a carbohydrate. According to an embodiment, said carbohydrate comprises a monosaccharide, a disaccharide, an oligosaccharide, a polysaccharide or a combination thereof. According to an embodiment, said carbohydrate comprises hexose, pentose or mixtures thereof. According to an embodiment, said hexose comprises glucose, fructose or mixtures thereof. According to an embodiment, said pentose comprises xylose and arabinose or mixtures thereof. According to an embodiment, said carbohydrate comprises starch. According to an embodiment, said carbohydrate is a cellulosic sugar. According to an embodiment, said carbohydrate is derived from processing a cellulosic or a lignocellulosic material, e.g. acid or enzyme hydrolysis of such material, optionally after some pretreatment.

Said provided first feedstock is combined with provided nitrogen source to form said fermentation medium. According to an embodiment, said nitrogen sources comprises at least one ammonium salt, e.g. ammonium acetate, ammonium bicarbonate, ammonium chloride, ammonium nitrate, ammonium sulfate, diammonium phosphate or a combination thereof. According to an embodiment, said nitrogen source comprises at least one complex nitrogen sources. According to an embodiment, said complex nitrogen source is selected from the group consisting of yeast extract, corn water-insolubles, stillage, molasses, urea and combinations thereof.

According to an embodiment, said second feedstock comprises CO, $CO_2$, carbonate, bicarbonate, $H_2$, glycerol, methanol, formate, urea or mixtures thereof.

According to an embodiment, said providing a first feedstock comprises fractionating corn. According to an embodiment, said fractionating comprises at least one of liquefying, saccharifying, filtering, washing and drying. According to an embodiment, said fractionating comprises wet milling or dry milling. According to an embodiment, said providing a first feedstock comprises contacting at least one of solid matter, a dry solid matter or a suspension of solid matter with recycled aqueous solution. According to an embodiment, said providing a first feedstock comprises mixing an aqueous solution or an aqueous suspension of a solid matter with recycled aqueous solution.

According to an embodiment, said fractionating forms a carbohydrates-comprising aqueous solution. According to an embodiment, said fractionating-formed, carbohydrates-comprising aqueous solution comprises corn water-insoluble matter. According to an embodiment, said formed fermentation medium comprises corn water-insoluble matter. According to an embodiment, said formed fermentation broth comprises corn water-insoluble matter. According to an embodiment, said fermentation broth comprises at least 5 g/L of corn water-insoluble matter, at least 10 g/L, at least 20 g/L, at least 30 g/L at least 40 g/L, at least 50 g/L, at least 60 g/L, at least 70 g/L, or at least 80 g/L. According to an embodiment, said corn water-insoluble matter comprises at least one of proteins, peptides and fibers.

According to an embodiment, said providing a first feedstock comprises fractionating corn, said first feedstock comprises at least one corn nitrogen compound and said corn nitrogen compound provides at least a fraction of said nitrogen source. According to an embodiment, said corn nitrogen compound comprises at least one amino acid.

The provided method comprises, according to an embodiment, providing an isolated organism capable of metabolizing $CO_2$ into acetyl-CoA. According to an embodiment, said organism is selected from the group consisting of *Clostridium ljungdahlii*, *Clostridium autoethanogenum*, *Clostridium ragsdalei*, *Eubacterium limosum*, *Butyribacterium methylotrophicum*, *Moorella thermoacetica*, *Clostridium aceticum*, *Acetobacterium woodii*, *Alkalibaculum bacchii*, *Clostridium drakei*, *Clostridium carboxidivorans*, *Clostridium formicoaceticum*, *Clostridium scatologenes*, *Moorella thermoautotrophica*, *Acetonema longum*, *Blautia producta*, *Clostridium glycolicum*, *Clostridium magnum*, *Clostridium mayombei*, *Clostridium methoxybenzovorans*, *Oxobacter pfennigii*, *Thermoanaerobacter kivui*, *Sporomusa ovata*, *Thermoacetogenium phaeum*, *Acetobacterium carbinolicum*, *Sporomusa termitida*, *Moorella glycerini*, *Eubacterium aggregans*, *Treponema azotonutricium*, and *Terrisporobacter glycolicus*. According to an embodiment, said organism is genetically modified to have a primary alcohol dehydrogenase gene or a secondary alcohol dehydrogenase gene deleted from its genome. According to an embodiment said organism is genetically modified to have a butanediol dehydrogenase gene deleted from its genome.

The nucleotide sequences disclosed herein are representative sequences and one of ordinary skill in the art will understand that variants of such sequences may also be utilized in methods as disclosed herein. For example, nucleotide sequences having at least 75%, 80%, 85%, 90%, 91%, 92%, 93%, 94%, 95%, 96%, 97%, 98%, or 99% identity to the nucleotide sequences included herein may be utilized.

The provided method further comprises, according to an embodiment, culturing said organism in a fermentor in said fermentation medium whereby said first feedstock and optionally said second feedstock are metabolized and a fermentation broth is formed, which broth comprises said bioproduct. According to an embodiment, at least 80% wt of said first feedstock is metabolized, at least 90% wt, at least 95% wt or at least 98% wt. According to an embodiment, both said first feedstock and said second feedstock are metabolized. According to an embodiment, at least 70% wt of said second feedstock is metabolized, at least 80% wt, at least 90% wt, at least 95% wt or at least 98% wt.

According to an embodiment, said first feedstock comprises a carbohydrate, and metabolizing said carbohydrate by said organism results in generating at least one of CO2 and hydrogen, which then provides at least a fraction of said second feedstock, e.g. at least 50%, at least 60%, at least 70%, at least 80% or at least 90%.

According to an embodiment, said metabolizing is conducted at a temperature in a range between 15° C. and 60° C., between 20° C. and 45° C., or between 27° C. and 37° C. According to an embodiment, said metabolizing is conducted at a pressure in a range between 0.1 bar and 3 bar, or between 0.6 bar and 2 bar. According to an embodiment, said metabolizing involves continuous fermentation. According to an embodiment, first feedstock concentration in said fermentor is in the range between 0 g/L and 150 g/L, between 1 g/L and 100 g/L or between 1.5 g/L and 60 g/L. According to an embodiment, said fermentation is anaerobic. According to an embodiment, said metabolizing is conducted at oxygen concentrations in a range between 1,000 ppm and 10,000 ppm, between 100 ppm and 1000 ppm, or between 0 ppm and 100 ppm.

According to an embodiment, said fermentation broth further comprises fermentation co-products. According to an embodiment, said bioproduct is acetone and said fermentation co-products comprise acetic acid, isopropanol, ethanol, 3-hydroxy-butyric acid and lactic acid. According to an embodiment, said bioproduct is isopropanol and said fermentation co-products comprise acetic acid, acetone, ethanol, 3-hydroxy-butyric acid and lactic acid. According to an embodiment, the weight/weight ratio between said co-product and said bioproduct is in range between 0.01 and 1. According to an embodiment, the ratio between said co-products and bioproduct in said fermentation broth is less than 1, less than 0.8, less than 0.6, less than 0.4 or less than 0.2. According to an embodiment, the ratio between said co-products and bioproduct in said fermentation broth is at least 0.01, at least 0.02, at least 0.05, at least 0.1, at least 0.2, or at least 0.3.

The provided method comprises, according to an embodiment, separating cells from said fermentation broth to form separated cells and recycling at least a fraction of said separated cells to the fermentor. Without wishing to be limited by theory, it seems that, said cell separating and cell recycling increases cell concentration in said fermentation broth. According to an embodiment, exponentially growing cells are separated from said fermentation broth and returned to the fermentor. According to an embodiment, separation of cells from said fermentation broth is initiated once the cell concentration is at least 0.1 g/L, at least 0.2 g/L, at least 0.5 g/L, or at least 1.0 g/L. According to an embodiment, separation and recycling of cells is maintained through the fermentation. According to an embodiment, said increased cell concentration is greater than 2 g/L, at least 5 g/L or at least 15 g/L. According to an embodiment, the amount of separated cells returned to the fermenter is at least 50%, at least 60%, at least 70%, at least 80%, at least 90%, or at least 100%.

Any form of cell separation is suitable. According to an embodiment, cell separation comprises removal of at least a fraction of said bioproduct, and optionally at least a fraction of at least one co-product, from the broth, e.g. by evaporation. According to an embodiment said bioproduct is removed from the broth at conditions which ensure the viability of the organism cells. According to an embodiment said bioproduct is removed from the broth, at least partially, by evaporating at sub-atmospheric pressure. According to an embodiment, said bioproduct is separated from the broth at a pressure in the range between 1 bar and 0.01 bar, between 0.9 bar and 0.1 bar, or between 0.5 bar and 0.15 bar. According to an embodiment, said bioproduct is separated from the broth at a temperature in the range, between 25° C. and 60° C., between 30° C. and 50° C., or between 35° C. and 40° C. According to an embodiment, said separating at least a fraction of said bioproduct generates a bioproduct-depleted stillage. According to an embodiment, at least a fraction of said bioproduct-depleted stillage is recycled to said fermentor.

According to an embodiment, said separating cells comprises filtering, whereby a retentate and a permeate are formed and said method further comprises recycling wherein at least a fraction of said retentate to the fermentor. According to an embodiment, said filtering comprises microfiltration. According to an embodiment, said microfiltration uses membranes with molecular weight cut-off greater than 10 kDa. According to an embodiment, said microfiltration uses membranes with molecular weight cut-off less than 100 kDa.

According to an embodiment, both said fermentation broth and said retentate comprise corn water-insoluble matter. According to an embodiment, said retentate comprises cells and corn water-insoluble matter at cell to insoluble matter weight/weight ratio in a range between 10:1 and 1:10, between 5:1 and 1:5 or between 3:1 and 1:4. According to an embodiment, said filtering and retentate recycling increases the concentration of corn water-insoluble matter in said fermentation broth. According to an embodiment, the concentration of corn water-insoluble matter in said fermentation broth is at least 5 g/L, at least 10 g/L, at least 20 g/L, at least 30 g/L at least 40 g/L, at least 50 g/L, at least 60 g/L, at least 70 g/L, or at least 80 g/L.

The provided method comprises, according to an embodiment, separating at least a fraction of said bioproduct to form separated bioproduct. Any form of separating is suitable for example, extracting, membrane separation or evaporating. According to an embodiment, said separating comprises evaporating to form a vapor phase comprising said bioproduct. According to an embodiment, said evaporating comprises distillation. According to an embodiment, said method further comprises condensing said vapor phase to form liquid bioproduct. According to an embodiment, the method further comprises refining said bioproduct. According to an embodiment, said refining comprises distilling.

According to an embodiment, said evaporating is conducted at a temperature in the range between 30° C. and 90° C., between 45° C. and 75° C. or between 50° C. and 65° C.

According to an embodiment, said evaporating is conducted at a pressure in the range between 0.05 bar and 3 bar, between 0.1 bar and 2 bar, or between 0.2 bar and 1.5 bar.

According to an embodiment, said separating at least a fraction of said bioproduct generates a bioproduct-depleted stillage. According to an embodiment, at least a fraction of said bioproduct-depleted stillage is recycled to said fermentor.

According to an embodiment, said vapor phase further comprises $CO_2$, and the method further comprising separating at least a fraction of the $CO_2$ from said bioproduct to form separated $CO_2$ and recycling said separated $CO_2$ to said fermentor. According to an embodiment, said separated $CO_2$ is pressurized prior to said recycle or simultaneously with it. According to an embodiment, said recycled $CO_2$ provides at least a fraction of said second feedstock. According to an embodiment, said separating $CO_2$ from bioproduct comprises condensing said bioproduct.

According to an embodiment, said bioproduct is separated, at least partially, by evaporating from said permeate.

It was found that said cell recycle helps overcoming substrate inhibition during fermentations. In the absence of cell recycling, substrate inhibition is observed above 15 g/L of sugar resulting in very low growth rates and low product titer. This substrate inhibition is not observed with cell recycle, reaching cell mass concentrations of e.g. greater than 10 g/L. Furthermore, the cell recycle mode of operation using microfiltration membranes allows the continuous removal of fermentation primary and secondary metabolites that are inhibitory to the cells. According to an embodiment, said provided first feedstock comprises carbohydrates at a concentration of at least 30 g/L, at least 50 g/L at least 70 g/L, at least 100 g/L or at least 130 g/L. According to an embodiment, the carbohydrates are rapidly metabolized, so that the concentration of carbohydrates in said fermentation broth is less than 10 g/L, less than 5 g/L, less than 3 g/L, less than 2 g/L, or less than 1 g/L, According to an embodiment, carbohydrate concentration in said provided first feedstock is in the range between 100 g/L and 150 g/L and cell concentration in said fermentation broth is in the range between 10 g/L and 20 g/L.

According to an embodiment, said evaporating forms bioproduct-depleted thin stillage and the method further comprises recycling said stillage to said providing a first feedstock, to said providing a second feedstock or to both. According to an embodiment, said providing a first feedstock comprises fractionating corn, and the method further comprises using said thin stillage in said fractionating, e.g. in wetting solids, washing solids or both. According to an embodiment, said providing a first feedstock comprises diluting and the method further comprises using said thin stillage in said diluting.

According to an embodiment, said evaporating forms bioproduct-depleted thin stillage and said thin stillage comprises an organic acid, further comprising recycling said organic acid to said fermentor, wherein said organic acid is metabolized. According to an embodiment, said recycling comprises separating said organic acid from said stillage. According to an additional or alternative embodiment, said recycling comprises using said stillage in providing said first feedstock, said first feedstock comprises at least a fraction of said organic acid and said fermentation medium comprises at least a fraction of said organic acid. According to an embodiment, said recycled organic acid is metabolized, at least partially to said bioproduct. According to an embodiment, the concentration of said organic acid in said fermentation broth is in the range between 0.1 g/L and 10 g/L, between 0.5 g/L and 8 g/L or between 1 g/L and 4 g/L. According to an embodiment, said organic acid comprises acetic acid.

According to an embodiment, acetic acid provides feedstock for the production of acetone or isopropanol. According to an embodiment, acetic acid that is added to the fermentation medium, e.g. with a nutrient or a carbohydrate stream or recycled from a downstream purification process. According to an embodiment, said added acetic acid is utilized, at least partially, by said microorganism to produce acetone or isopropanol. According to an embodiment, utilization of this acetic acid results in a further increase in mass yields based on first feedstock of either acetone or isopropanol. According to an embodiment, increases in mass yields from first feedstock could even surpass the theoretical maximum values.

According to an embodiment, wherein said evaporating forms bioproduct-depleted thin stillage, the method further comprises drying said thin stillage to form a thick stillage and evaporated process water, which evaporated process water comprises a fermentation co-product. According to an embodiment, said evaporated process water is used in said providing a first feedstock, in said providing a second feedstock or in both.

According to an embodiment, said providing a first feedstock comprises fractionating corn, and the method further comprises using said evaporated process water in said fractionating, e.g. in wetting solids, washing solids or both. According to an embodiment, said providing a first feedstock comprises diluting and the method further comprises using said evaporated process water in said diluting.

According to an embodiment, said co-product in evaporated process water is an organic acid and said method further comprises recycling said organic acid to said fermentor, wherein said organic acid is metabolized. According to an embodiment, said recycled organic acid is metabolized, at least partially to said bioproduct. According to an embodiment, the concentration of said organic acid in said fermentation broth is in the range between 0.1 g/L and 10 g/L, between 0.5 g/L and 8 g/L or between 1 g/L and 4 g/L. According to an embodiment, said organic acid comprises acetic acid.

According to an embodiment, said bioproduct is acetone, and the method further comprises catalytically converting said separated acetone into at least one acetone derivative. According to an embodiment, said acetone derivative is selected from mesitylene (1-3-5-trimethylbenzene), isophthalic acid, uvitic acid, meta-xylene and combinations thereof.

EXAMPLES

Example 1

Three plasmids were constructed: a plasmid control (with an empty expression cassette), plasmid #1 (expressing a first acetone production pathway comprising a thiolase (thl) gene from *C. acetobutylicum*, a CoA-transferase subunit A (ctfA) gene from *C. acetobutylicum*, a CoA-transferase subunit B (ctfB) gene from *C. acetobutylicum*, and an acetoacetate decarboxylase (adc) gene from *C. acetobutylicum*), and plasmid #2 (expressing a second acetone production pathway comprising a thiolase (thlA3) gene from *C. kluyveri*, a CoA-transferase subunit A (ctfA) gene from *C. acetobutylicum*, a CoA-transferase subunit B (ctfB) gene from *C. acetobutylicum*, and an acetoacetate decarboxylase (adc) gene from *C. acetobutylicum*). In addition, two strains of *C. ljungdahlii* were prepared: the wild-type (WT) strain and a gene deletion strain (ΔSADH) in which the native secondary alcohol dehydrogenase gene from *C. ljungdahlii* has been deleted. From these components a total of four strains were generated: WT with the plasmid control, WT with plasmid #1, ΔSADH with plasmid #1, and ΔSADH with plasmid #2.

The SADH and acetone production pathway nucleotide sequences are as set forth below:

```
Secondary alcohol dehydrogenase (SADH) gene
(CLJU_c24860) (SEQ ID NO: 1):
ATGAAAGGTTTTGCAATGTTAGGTATTAACAAATTAGGATGGATTGAAAA

GAAAAACCCAGTGCCAGGTCCTTATGATGCGATTGTACATCCTCTAGCTG

TATCCCCATGTACATCAGATATACATACGGTTTTTGAAGGAGCACTTGGT

AATAGGGAAAATATGATTTTAGGCCATGAAGCTGTAGGTGAAATAGCCGA

AGTTGGCAGCGAAGTTAAAGATTTTAAAGTTGGCGATAGAGTTATCGTAC

CATGCACAACACCTGACTGGAGATCTTTAGAAGTCCAAGCTGGTTTTCAG

CAGCATTCAAACGGTATGCTTGCAGGATGGAAGTTTTCCAATTTTAAAGA

TGGTGTATTTGCAGATTACTTTCATGTAAACGATGCAGATATGAATCTTG

CCATACTCCCAGATGAAATACCTTTAGAAAGTGCAGTTATGATGACAGAC

ATGATGACTACTGGTTTTCATGGAGCAGAACTTGCAGACATAAAAATGGG

CTCCAGCGTTGTAGTAATTGGTATAGGAGCTGTTGGATTAATGGGAATAG

CCGGTTCCAAACTTCGAGGAGCAGGCAGAATTATCGGTGTTGGAAGCAGA

CCTGTTTGTGTTGAAACAGCTAAATTTTATGGAGCAACTGATATTGTAAA

TTATAAAAATGGTGATATAGTTGAACAAATCATGGACTTAACTCATGGTA

AGGTGTAGACCGTGTAATTCATGGCAGGCGGTGGTGCTGAAACACTAGCA

CAAGCAGTAACTATGGTTAAACCTGGCGGCGTAATTTCTAACATCAACTA

CCATGGAAGCGGTGATACTTTACCAATACCTCGTGTTCAATGGGGCTGCG

GCATGGCTCACAAAACTATAAGAGGAGGATTATGCCCCGGCGGACGTCTT

AGAATGGAAATGCTAAGAGATCTTGTTCTATATAAACGTGTTGATTTGAG

TAAACTTGTTACTCATGTATTTGATGGTGCAGAAAATATTGAAAAGGCCC

TTTTGCTTATGAAAAATAAGCCAAAAGATTTAATTAAATCAGTAGTTACA

TTCTAA
```

Plasmid #1 (First) Acetone Production Pathway: Transcriptional Promoter from C. ljundgahlii Pta (CLJU c12770) Gene Thiolase (thl) gene from C. acetobutylicum
(CA_C2873) (SEQ ID NO: 2):
ATGAAAGAAGTTGTAATAGCTAGTGCAGTAAGAACAGCGATTGGATCTTA

TGGAAAGTCTCTTAAGGATGTACCAGCAGTAGATTTAGGAGCTACAGCTA

TAAAGGAAGCAGTTAAAAAAGCAGGAATAAAACCAGAGGATGTTAATGAA

GTCATTTTAGGAAATGTTCTTCAAGCAGGTTTAGGACAGAATCCAGCAAG

ACAGGCATCTTTTAAAGCAGGATTACCAGTTGAAATTCCAGCTATGACTA

TTAATAAGGTTTGTGGTTCAGGACTTAGAACAGTTAGCTTAGCAGCACAA

ATTATAAAAGCAGGAGATGCTGACGTAATAATAGCAGGTGGTATGGAAAA

TATGTCTAGAGCTCCTTACTTAGCGAATAACGCTAGATGGGATATAGAA

TGGGAAACGCTAAATTTGTTGATGAAATGATCACTGACGGATTGTGGGAT

GCATTTAATGATTACCACATGGGAATAACAGCAGAAAACATAGCTGAGAG

ATGGAACATTTCAAGAAGAACAAGATGAGTTTGCTCTTGCATCACAAA

AAAAAGCTGAAGAAGCTATAAAATCAGGTCAATTTAAAGATGAAATAGTT

CCTGTAGTAATTAAAGGCAGAAAGGGAGAAACTGTAGTTGATACAGATGA

GCACCCTAGATTTGGATCAACTATAGAAGGACTTGCAAAATTAAAACCTG

CCTTCAAAAAAGATGGAACAGTTACAGCTGGTAATGCATCAGGATTAAAT

GACTGTGCAGCAGTACTTGTAATCATGAGTGCAGAAAAAGCTAAAGAGCT

TGGAGTAAAACCACTTGCTAAGATAGTTTCTTATGGTTCAGCAGGAGTTG

ACCCAGCAATAATGGGATATGGACCTTTCTATGCAACAAAAGCAGCTATT

GAAAAAGCAGGTTGGACAGTTGATGAATTAGATTTAATAGAATCAAATGA

AGCTTTTGCAGCTCAAAGTTTAGCAGTAGCAAAAGATTTAAAATTTGATA

TGAATAAAGTAAATGTAAATGGAGGAGCTATTGCCCTTGGTCATCCAATT

GGAGCATCAGGTGCAAGAATACTCGTTACTCTTGTACACGCAATGCAAA

AAGAGATGCAAAAAAAGGCTTAGCAACTTTATGTATAGGTGGCGGACAAG

GAACAGCAATATTGCTAGAAAAGTGCTAG

CoA-transferase subunit A (ctfA) gene from C.
acetobutylicum (CA_P0163) (SEQ ID NO: 3):
ATGAACTCTAAAATAATTAGATTTGAAAATTTAAGGTCATTCTTTAAAGA

TGGGATGACAATTATGATTGGAGGTTTTTTAAACTGTGGCACTCCAACCA

AATTAATTGATTTTTAGTTAATTTAAATATAAAGAATTTAACGATTATA

AGTAATGATACATGTTATCCTAATACAGGTATTGGTAAGTTAATATCAAA

TAATCAAGTAAAAAAGCTTATTGCTTCATATATAGGCAGCAACCCAGATA

CTGGCAAAAAACTTTTTAATAATGAACTTGAAGTAGAGCTCTCTCCCCAA

GGAACTCTAGTGGAAAGAATACGTGCAGGCGGATCTGGCTTAGGTGGTGT

ACTAACTAAAACAGGTTTAGGAACTTTGATTGAAAAAGGAAAGAAAAAA

TATCTATAAATGGAACGGAATATTTGTTAGAGCTACCTCTTACAGCCGAT

GTAGCATTAATTAAAGGTAGTATTGTAGATGAGGCCGGAAACACCTTCTA

TAAAGGTACTACTAAAAACTTTAATCCCTATATGGCAATGGCAGCTAAAA

CCGTAATAGTTGAAGCTGAAAATTTAGTTAGCTGTGAAAAACTAGAAAAG

GAAAAAGCAATGACCCCCCGGAGTTCTTATAAATTATATAGTAAAGGAGCC

TGCATAA

CoA-transferase subunit B (ctfB) gene from C.
acetobutylicum (CA_P0164) (SEQ ID NO: 4):
ATGATTAATGATAAAAACCTAGCGAAAGAAATAATAGCCAAAAGAGTTGC

AAGAGAATTAAAAAATGGTCAACTTGTAAACTTAGGTGTAGGTCTTCCTA

CCATGGTTGCAGATTATATACCAAAAAATTTCAAAATTACTTTCCAATCA

GAAAACGGAATAGTTGGAATGGGCGCTAGTCCTAAAATAAATGAGGCAGA

TAAAGATGTAGTAAATGCAGGAGGAGACTATACAACAGTACTTCCTGACG

GCACATTTTTCGATAGCTCAGTTTCGTTTTCACTAATCCGTGGTGGTCAC

GTAGATGTTACTGTTTTAGGGGCTCTCCAGGTAGATGAAAAGGGTAATAT

AGCCAATTGGATTGTTCCTGGAAAAATGCTCTCTGGTATGGGTGGAGCTA

TGGATTTAGTAAATGGAGCTAAGAAAGTAATAATTGCAATGAGACATACA

AATAAAGGTCAACCTAAAATTTTAAAAAAATGTACACTTCCCCTCACGGC

AAAGTCTCAAGCAAATCTAATTGTAACAGAACTTGGAGTAATTGAGGTTA

TTAATGATGGTTTACTTCTCACTGAAATTAATAAAAACACAACCATTGAT

GAAATAAGGTCTTTAACTGCTGCAGATTTACTCATATCCAATGAACTTAG

ACCCATGGCTGTTTAG

Acetoacetate decarboxylase (adc) gene from C.
acetobutylicum (CA_P0165) (SEQ ID NO: 5):
ATGTTAAAGGATGAAGTAATTAAACAAATTAGCACGCCATTAACTTCGCC

TGCATTTCCTAGAGGACCCTATAAATTTCATAATCGTGAGTATTTTAACA

TTGTATATCGTACAGATATGGATGCACTTCGTAAAGTTGTGCCAGAGCCT

TTAGAAATTGATGAGCCCTTAGTCAGGTTTGAAATTATGGCAATGCATGA

TACGAGTGGACTTGGTTGTTATACAGAAAGCGGACAGGCTATTCCCGTAA

GCTTTAATGGAGTTAAGGGAGATTATCTTCATATGATGTATTTAGATAAT

GAGCCTGCAATTGCAGTAGGAAGGGAATTAAGTGCATATCCTAAAAAGCT

CGGGTATCCAAAGCTTTTTGTGGATTCAGATACTTTAGTAGGAACTTTAG

ACTATGGAAAACTTAGAGTTGCGACAGCTACAATGGGGTACAAACATAAA

GCCTTAGATGCTAATGAAGCAAAGGATCAAATTTGTCGCCCTAATTATAT

GTTGAAAATAATACCCAATTATGATGGAAGCCCTAGAATATGTGAGCTTA

TAAATGCGAAAATCACAGATGTTACCGTACATGAAGCTTGGACAGGACCA

ACTCGACTGCAGTTATTTGATCACGCTATGGCGCCACTTAATGATTTGCC

AGTAAAAGAGATTGTTTCTAGCTCTCACATTCTTGCAGATATAATATTGC

CTAGAGCTGAAGTTATATATGATTATCTTAAGTAA

Plasmid #2 (Second) Acetone Production Pathway: Transcriptional Promoter from C. ljundgahlii Pta (CLJU c12770) Gene Thiolase (thlA3) gene from C. kluyveri
(CKL_3698) (SEQ ID NO: 6):
ATGAGAGAAGTAGTTATTGTAAGTGCAGTGAGAACAGCTATAGGAAGTTT

CGGTGGAACTTTGAAAGATGTTCCAGCAGTGGAATTAGGAGCTGTAGTTA

TAAAAGAAGCAGTAAAAAGAGCAAATGTTAAGCCAGAACAAATAGATGAA

GTTATATTTGGAAACGTAATACAGGCAGGTCTTGGTCAGAGTCCAGCGAG

-continued
```
ACAGGCAGCTGTAAAAGCAGGTATTCCTGTAGAAGTTCCAGCATTCACAT

TAAATAAGGTTTGTGGTTCAGGACTTAGATCAGTAAGTTTGGCAGCTCAG

GTTATAAAAGCTGGAGATGCTGATATTGTCGTAGTTGGTGGAATGGAAAA

CATGTCTGCTGCTCCATATGTACTCCCAAAAGCTAGATGGGGACATAGAA

TGGGAGAAGGAAAAATAGTTGATGCTATGATAAAAGACGGACTTTGGGAG

GCATTCAACAATTATCACATGGGAATTACAGCTGAAAACATAGCAGAAAA

ATGGGGTTTAACAAGAGAAGAGCAGGATGAATTTTCAGCAGCGTCCCAGC

AAAAAGCAGAAGCAGCTCAAAAAGCAGGTAAATTCAAAGATGAAATAGTT

CCAGTAACTGTTAAGATAAAAAGAAAGAAGTAGTTTTTGATACTGATGA

GTATATAAAACCAGGAACAACTGTTGAAACACTGGCAAAATTGAGACCAG

CATTCAAAAAGATGGAACAGTTACAGCAGGTAATGCTTCAGGAATAAAT

GATGCAGCAGCAGCTTTAGTTGTGATGAGTGCAGATAAGGCAAAAGAACT

TGGAATTAAACCACTTGCAAAGATTGTTTCCTATGGAAGTGCAGGATTAG

ATCCGACAATAATGGGATATGGTCCTTTCCATGCAACAAAAGCAGCACTT

GAAAAAGCTAACTTGTCAGTTGCAGATTTAGACTTAATAGAAGCAAATGA

AGCATTCGCTTCACAGAGTTTGGCAGTAGCAAAAGATTTAGAATTTGATA

TGAGCAAAGTAAATGTAAATGGAGGAGCAATAGCTCTTGGACATCCAGTT

GGAGCATCAGGAGCAAGAATACTTGTTACATTACTTCATGAAATGCAGAG

AAGAGATGCAAAAAAGGTCTTGCAACATTATGTATAGGCGGTGGAATGG

GAACTGCTTTAATAGTAGAGAGATAA

CoA-transferase subunit A (ctfA) gene from C.
acetobutylicum (CA_P0163) (SEQ ID NO: 7):
ATGAACTCTAAAATAATTAGATTTGAAAATTTAAGGTCATTCTTTAAAGA

TGGGATGACAATTATGATTGGAGGTTTTTTAAACTGTGGCACTCCAACCA

AATTAATTGATTTTTTAGTTAATTTAAATATAAAGAATTTAACGATTATA

AGTAATGATACATGTTATCCTAATACAGGTATTGGTAAGTTAATATCAAA

TAATCAAGTAAAAAAGCTTATTGCTTCATATATAGGCAGCAACCCAGATA

CTGGCAAAAAACTTTTTAATAATGAACTTGAAGTAGAGCTCTCTCCCAA

GGAACTCTAGTGGAAAGAATACGTGCAGGCGGATCTGGCTTAGGTGGTGT

ACTAACTAAAACAGGTTTAGGAACTTTGATTGAAAAAGGAAAGAAAAAAA

TATCTATAAATGGAACGGAATATTTGTTAGAGCTACCTCTTACAGCCGAT

GTAGCATTAATTAAAGGTAGTATTGTAGATGAGGCCGGAAACACCTTCTA

TAAAGGTACTACTAAAAACTTTAATCCCTATATGGCAATGGCAGCTAAAA

CCGTAATAGTTGAAGCTGAAAATTTAGTTAGCTGTGAAAAACTAGAAAAG

GAAAAAGCAATGACCCCCGGAGTTCTTATAAATTATATAGTAAAGGAGCC

TGCATAA

CoA-transferase subunit B (ctfB) gene from C.
acetobutylicum (CA_P0164) (SEQ ID NO: 8):
ATGATTAATGATAAAAACCTAGCGAAAGAAATAATAGCCAAAAGAGTTGC

AAGAGAATTAAAAAATGGTCAACTTGTAAACTTAGGTGTAGGTCTTCCTA

CCATGGTTGCAGATTATATACCAAAAAATTTCAAAATTACTTTCCAATCA

GAAAACGGAATAGTTGGAATGGGCGCTAGTCCTAAAATAAATGAGGCAGA

TAAAGATGTAGTAAATGCAGGAGGAGACTATACAACAGTACTTCCTGACG

GCACATTTTTCGATAGCTCAGTTTCGTTTTCACTAATCCGTGGTGGTCAC

GTAGATGTTACTGTTTTAGGGGCTCTCCAGGTAGATGAAAAGGGTAATAT

AGCCAATTGGATTGTTCCTGGAAAAATGCTCTCTGGTATGGGTGGAGCTA

TGGATTTAGTAAATGGAGCTAAGAAAGTAATAATTGCAATGAGACATACA

AATAAAGGTCAACCTAAAATTTTAAAAAAATGTACACTTCCCCTCACGGC

AAAGTCTCAAGCAAATCTAATTGTAACAGAACTTGGAGTAATTGAGGTTA

TTAATGATGGTTTACTTCTCACTGAAATTAATAAAAACACAACCATTGAT

GAAATAAGGTCTTTAACTGCTGCAGATTTACTCATATCCAATGAACTTAG

ACCCATGGCTGTTTAG

Acetoacetate decarboxylase (adc) gene from C.
acetobutylicum (CA_P0165) (SEQ ID NO: 9):
ATGTTAAAGGATGAAGTAATTAAACAAATTAGCACGCCATTAACTTCGCC

TGCATTTCCTAGAGGACCCTATAAATTTCATAATCGTGAGTATTTTAACA

TTGTATATCGTACAGATATGGATGCACTTCGTAAAGTTGTGCCAGAGCCT

TTAGAAATTGATGAGCCCTTAGTCAGGTTTGAAATTATGGCAATGCATGA

TACGAGTGGACTTGGTTGTTATACAGAAAGCGGACAGGCTATTCCCGTAA

GCTTTAATGGAGTTAAGGGAGATTATCTTCATATGATGTATTTAGATAAT

GAGCCTGCAATTGCAGTAGGAAGGGAATTAAGTGCATATCCTAAAAAGCT

CGGGTATCCAAAGCTTTTTGTGGATTCAGATACTTTAGTAGGAACTTTAG

ACTATGGAAAACTTAGAGTTGCGACAGCTACAATGGGGTACAAACATAAA

GCCTTAGATGCTAATGAAGCAAAGGATCAAATTTGTCGCCCTAATTATAT

GTTGAAAATAATACCCAATTATGATGGAAGCCCTAGAATATGTGAGCTTA

TAAATGCGAAAATCACAGATGTTACCGTACATGAAGCTTGGACAGGACCA

ACTCGACTGCAGTTATTTGATCACGCTATGGCGCCACTTAATGATTTGCC

AGTAAAAGAGATTGTTTCTAGCTCTCACATTCTTGCAGATATAATATTGC

CTAGAGCTGAAGTTATATATGATTATCTTAAGTAA
```

All four strains were grown in standard PETC medium with 5 g/l of fructose and 5 µg/ml of clarithromycin at 37° C. and under anaerobic conditions. Cultures were grown in glass test tubes with tightened caps for 7 days after inoculation.

FIG. 1 shows the end point metabolite profile along with the mass yield of total products and the mass yield of acetone. Acetone mass yield was calculated by determining how much acetone was generated (g/l) and dividing by the total substrates consumed (g/l). Total substrates consumed is the amount of both fructose and ethanol consumed by the strain. Total mass yield was calculated by determining total products generated (acetone, IPA, 3-HB, and acetate) and dividing by the total substrates (fructose and ethanol) consumed.

WT with the plasmid control (FIG. 1A) produced only acetate with a mass yield of 99 wt %, which accounts of 99% of all carbon from the sugar. The WT strain with plasmid #1 (FIG. 1B) produced acetic acid, isopropanol, 3-hydroxybutyric acid, and acetone, with a total mass yield of 93 wt %. Though acetone was produced, it was the most minor metabolite with a mass yield of only 2 wt %. This was because of a native secondary alcohol dehydrogenase in *C. ljungdahlii* causing reduction of acetone into isopropanol and acetoacetate (an intermediate to acetone) into 3-hydroxybutyric acid. This gene was deleted from the chromosome of *C. ljungdahlii*, generating the strain ΔSADH. Plasmid #1 was then introduced into the ΔSADH strain (FIG. 1C). ΔSADH with plasmid #1 mainly only produced acetic acid and acetone, with trace amounts of isopropanol and 3-hydroxybutyric acid. The overall mass yield was 80 wt %, and the mass yield for acetone increased to 19 wt %. Finally, plasmid #2 was generated with an enhanced acetone pathway and introduced into the ΔSADH strain (FIG. 1D). In this strain, acetone became the primary metabolite with a mass yield of 43 wt %. Acetic acid was also produced with trace amounts of isopropanol and 3-hydroxybutyric acid. The total mass yield was 55 wt %. The 43 wt % yield is about 140% the theoretical maximum yield for acetone without mixotrophy, clearly demonstrating the enhanced mass yield.

Example 2

An experiment was performed comparing cell recycle mode of operation and batch mode (no cell recycle) using *C. lungdahlii* ΔSADH with plasmid #2. Experiments were conducted at 37° C. with pH control at 5.5 using 30% NH$_4$OH under anaerobic conditions. For no cell recycle (batch) mode, the sterile medium (modified PETC medium) was added to the fermenter and the process was started by inoculating actively growing cells from a seed rector. The pH was controlled by adding NH$_4$OH. However, in cell recycle mode of operation the fermentation tank was continuously fed the modified PETC medium at a dilution rate of 0.3 h$^{-1}$ of batch mode operation and the contents of the reactor were pumped through a microfiltration membrane, which separated the retentate containing microbial cells from the permeate (cell-free media). The retentate was recycled back to the fermenter. The modified PETC medium included 5 g/L of yeast extract and 15 g/L of fructose was used for this experiment. The fructose concentration in the feed for cell recycle experiment was changed to 50 g/L after 64 h of elapsed fermentation time (EFT).

Figure 2:
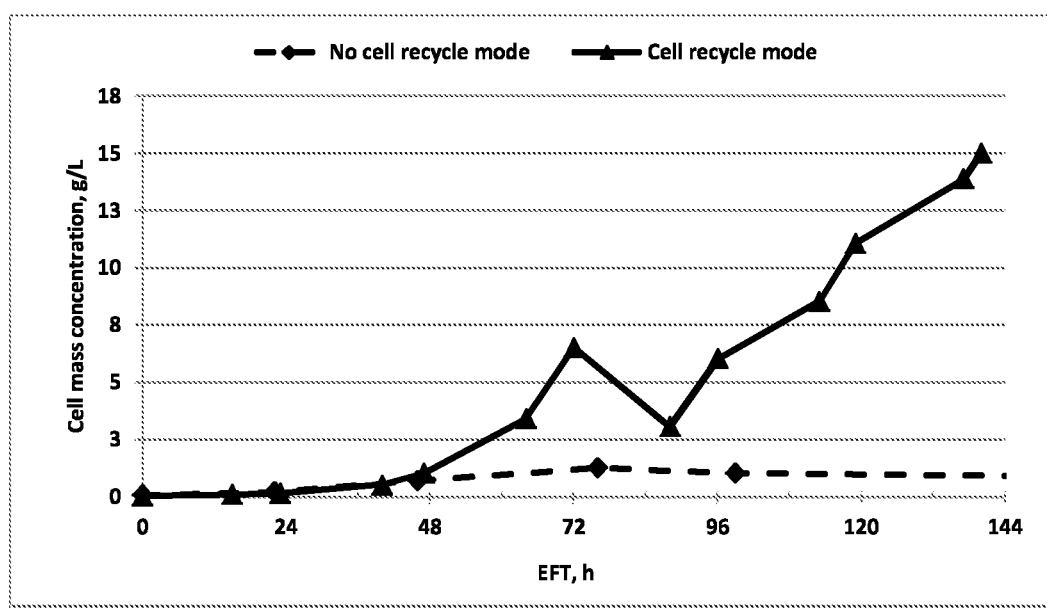
FIG. 2. Cell mass concentrations obtained with and without cell recycle mode. With cell recycle mode, the operation was shifted from no cell recycle (batch) to cell recycle mode of operation after 40 h of fermentation.

FIG. 2 compares no cell recycle (batch) mode with cell recycle mode of operation. During the cell recycle experiment, the fermenter was run in batch (no cell recycle) mode until 46 h before switching to cell recycle mode. Hence, the cell mass concentration of cell recycle mode was only 1 g/L for the first 40 h of operation. After 40 h, the cell mass concentration in the cell recycle mode began to build up and reached up to 15 g/L of cells by 144 h of EFT. On the other hand, the maximum cell mass concentrations achieved in no cell recycle (batch) mode was only 1.3 g/L. This demonstrates that the *C. lungdahlii* ΔSADH with plasmid #2 containing cells can be grown to very high cell densities with cell recycle mode of operation.

Figure 3:
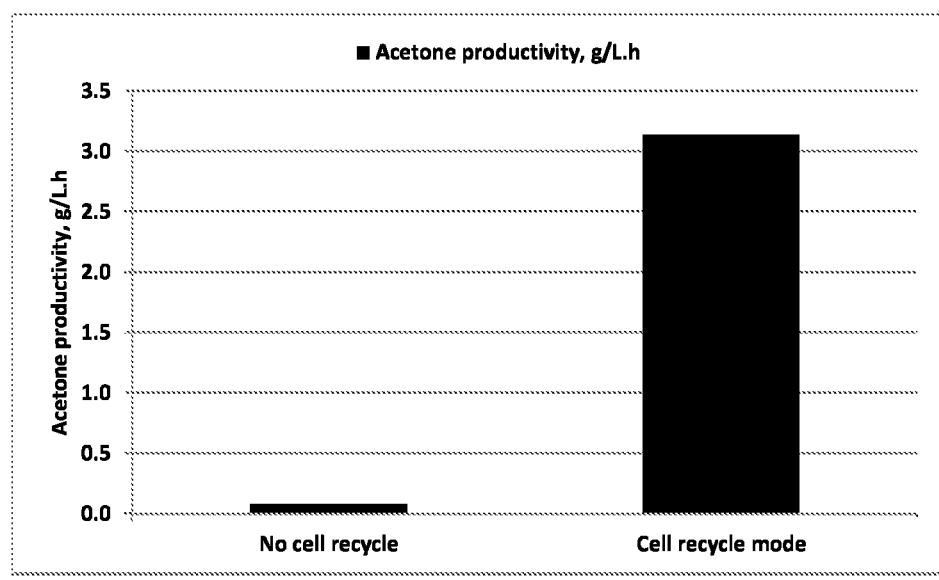
FIG. 3. Acetone productivity with and without cell recycle mode of operation.
Figure 4:
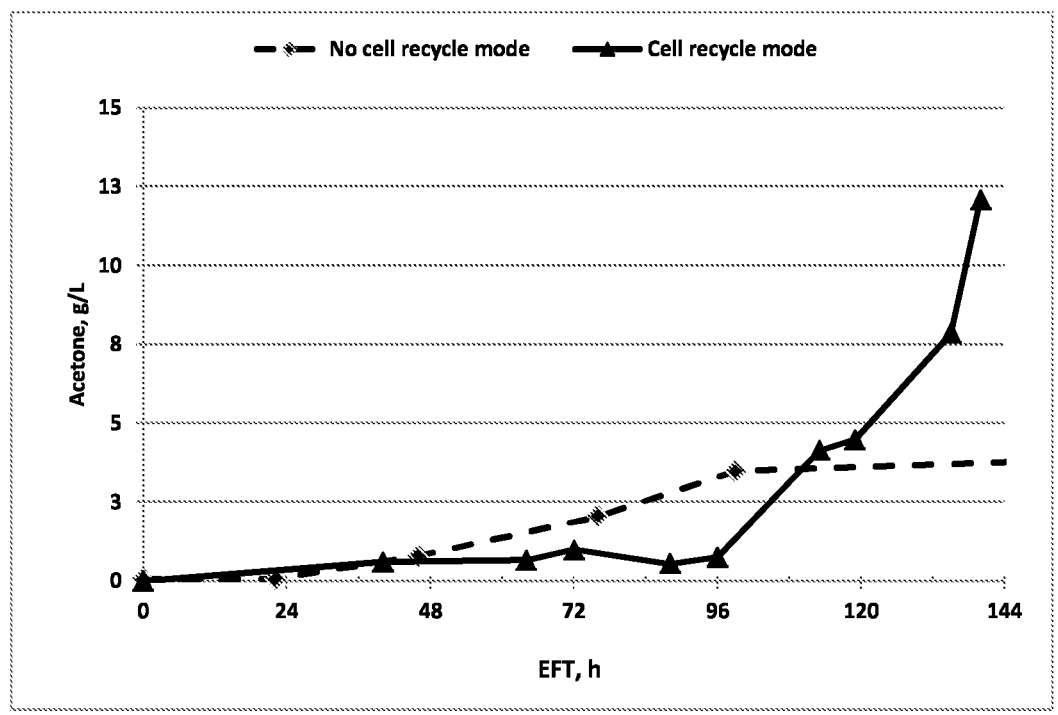
FIG. 4. Acetone titers with and without cell recycle mode of operation. With cell recycle mode, the operation was shifted from no cell recycle (batch) to cell recycle mode of operation after 40 h of fermentation. The feed fructose concentration from 40 h to 64 h was 15 g/L and from 64 h to 140 h was 50 g/L.

FIGS. 3 and 4 show the improvement in acetone productivity and acetone concentration with cell recycle mode of operation and compares it with no cell recycle (batch mode). The maximum productivity of acetone in batch mode was observed to be 0.08 g/L/h. With cell recycle mode, the highest productivity of acetone increased by 39 fold, resulting in 3.1 g/L/h acetone productivity. Cell recycle mode of operation helped achieving 250% more acetone titers in comparison to no cell recycle (batch) mode (12.1 g/L in cell recycle mode versus 3.5 g/L in batch mode). Hence, the cell recycle mode of operation clearly demonstrates significant improvement in acetone productivity and acetone titers when compared to no cell recycle (batch) fermentations.

Example 3

The acetone producing strain *C. lungdahlii* ΔSADH with plasmid #2 was grown in a cell recycle fermentation process. The strain was grown in modified PETC medium to mid-exponential phase (OD$_{600nm}$ of 0.8-1.5) and then used to inoculate a 3 L bioreactor with a 1.9 L working volume of modified PETC medium (5 g/L yeast extract, 5 g/L fructose, and 5 µg/mL clarithromycin). After inoculation, the culture was sparged with N$_2$ for the first 24 hours to maintain anaerobic conditions. The culture was conducted at 37° C., and the pH was controlled from dropping below 5.0 using 4M NH$_4$OH. After the culture reached an OD$_{600nm}$ of 1.5, the cell recycle was initiated. Feed and permeate rates were balanced to maintain a constant working volume and the average rates were 3-6 mL/min. A 0.15 ft$^2$, 0.1 µm sintered stainless steel microfiltration membrane from Graver Technologies was used to accomplish cell recycle. The feed rate to the membrane was 150 mL/min, and the recirculation rate was 6.5 L/min. The retentate rate was between 144-147 mL/min, which equaled the membrane feed rate minus the permeate rate. The culture was in complete cell recycle mode until the OD$_{600nm}$ reached 35-60, at which time a harvest was started that was equal to the critical dilution rate that maintained a constant cell density in the fermenter. Fructose concentration in the feed was increased to as high at 80 g/L during the course of building cell density, and the concentration of clarithromycin was maintained at 5 µg/mL.

Figure 5:
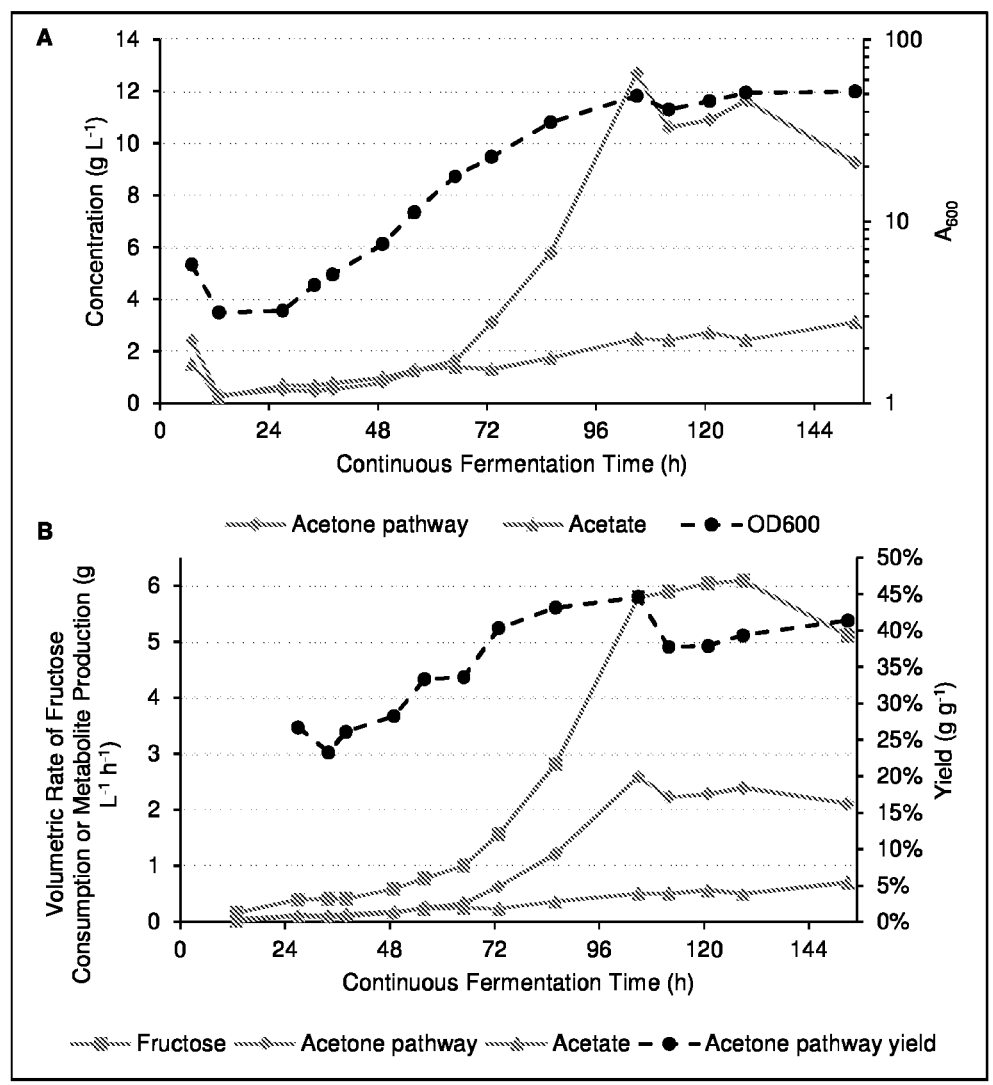
FIG. 5. Cell recycle acetone fermentation. Fermentation performance for 150 hours of cell retention fermentation. At hour 86, a harvest was initiated to maintain a constant cell density. Titers and cell densities (A) are shown in addition to volumetric productivities and the total acetone pathway (acetone, 3-HB, and IPA) product yield (B). A, Acetone pathway titers (diamonds), acetate titers (triangles) and cell densities (circles with broken line). B, Fructose volumetric consumption (squares), acetone pathway volumetric productivity (diamonds), acetate volumetric productivity (triangles), and acetone pathway mass yield (%-g/g) from consumed fructose (circles with broken line). Individual product and fructose titers are shown in FIG. 6.
Figure 6:
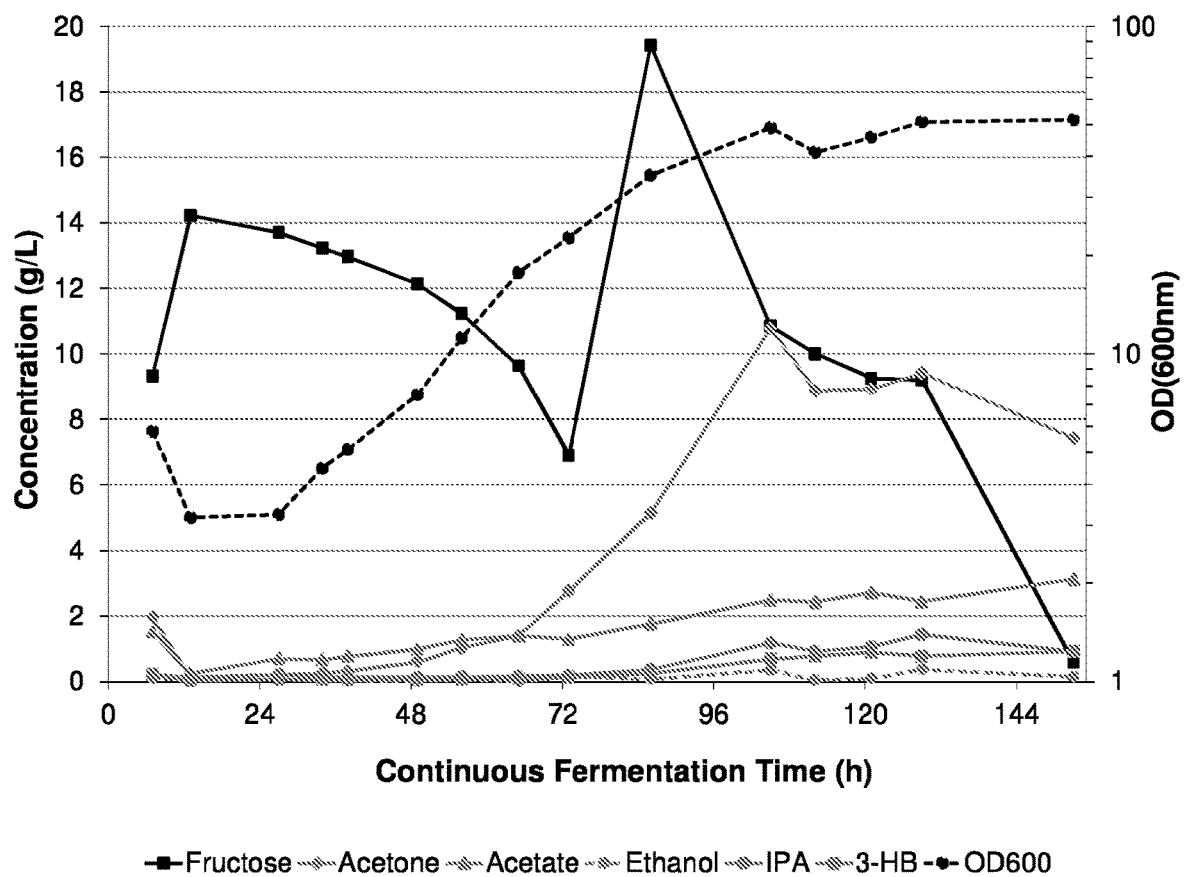
FIG. 6. Cell recycle acetone fermentation profiles. Residual fructose concentration (black squares), acetone (diamonds), acetate (triangles), ethanol (dashed grey circles), IPA (solid grey circles), 3-HB (grey squares), and cell density (OD600 nm—dashed black circles).

As shown in FIG. 5A, the targeted cell densities were reached in approximately 100 hours after cell retention was started, at which point a harvest was implemented to maintain a constant cell density. Also at this point, the maximum acetone pathway (i.e., acetone, 3-HB, and IPA) titers were achieved of 12.7 g/L with concurrent acetate titers of 2.5 g/L. A minor amount of ethanol (0.05-0.78 g/L, FIG. 6) was also produced. Acetone concentrations reached a maximum of 10.8 g/L (FIG. 6), which was 85% of the total mass of acetone pathway products. Also shown in FIG. 5*b*, starting at hour 85 and for 65 hours afterwards (i.e., up to 150 h continuous fermentation time), volumetric productivities of acetone pathway products and acetate remained essentially constant, along with fructose volumetric consumption. The average volumetric productivity of acetone pathway products and acetate was 2.32 and 0.56 g/L/h, respectively, and the average fructose volumetric consumption rate was 5.78 g/L/h. This resulted in an average acetone pathway yield of 40.1 wt % (~87% of the theoretical mixotrophic maximum). Real-time acetone pathway mass yields ranged from 37.8 to 44.6 wt % during this time period (FIG. 5B).

Example 4

Figure 7:
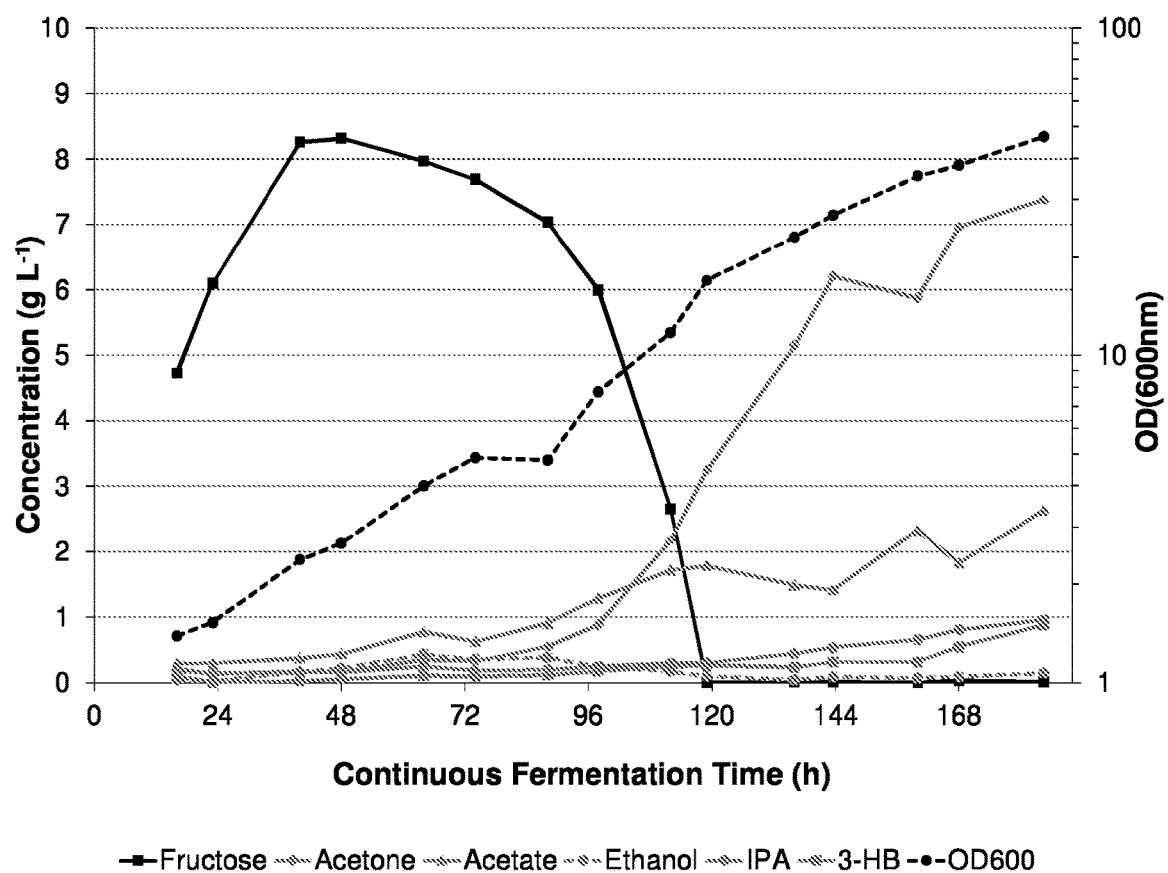
FIG. 7. Cell recycle acetone fermentation profiles. Residual fructose concentration (black squares), acetone (grey diamonds), acetate (grey triangles), ethanol (dashed grey circles), IPA (solid grey circles), 3-HB (grey squares), and cell density (OD600 nm—dashed black circles).

A biological replicate fermentation of Example 3 was prepared and run in a similar manner. Fermentation profiles are shown in FIG. 7. In this fermentation, the OD$_{600nm}$ reached 46 with total acetone pathway products of 9.2 g/L (7.4 g/L acetone and 0.9 g/L of 3-HB and IPA both).

The invention claimed is:

1. A method for producing a bioproduct selected from acetone, isopropanol and a combination thereof, comprising
(i) providing a first feedstock, a nitrogen source and optionally a second feedstock to form a fermentation medium;
(ii) providing an isolated organism capable of metabolizing $CO_2$ into acetyl-CoA;
(iii) culturing said organism in a fermenter in said fermentation medium whereby said first feedstock and optionally said second feedstock are metabolized and a fermentation broth is formed, which broth comprises said bioproduct;
(iv) separating cells from said fermentation broth to form separated cells;
(v) recycling at least a fraction of said separated cells to the fermenter; and
(vi) separating said bioproduct to form separated bioproduct;
which producing is characterized by one or more of the following criteria
a. cell concentration in said fermenter being greater than 2 g/L;
b. mass yield on first feedstock being greater than 32%;
c. productivity being greater than 0.12 g/L/h; and
d. total bioproduct titer being greater than 10 g/L.

2. A method according to claim 1, wherein said bioproduct is acetone.

3. A method according to claim 1, wherein said bioproduct is isopropanol.

4. A method according to claim 1 characterized by at least two of said criteria.

5. A method according to claim 1 characterized by at least three of said criteria.

6. A method according to claim 1 characterized by said four criteria.

7. A method according to claim 1, wherein said organism is selected from the group consisting of *Clostridium ljungdahlii, Clostridium autoethanogenum, Clostridium ragsdalei, Eubacterium limosum, Butyribacterium methylotrophicum, Moorella thermoacetica, Clostridium aceticum, Acetobacterium woodii, Alkalibaculum bacchii, Clostridium drakei, Clostridium carboxidivorans, Clostridium formicoaceticum, Clostridium scatologenes, Moorella thermoautotrophica, Acetonema longum, Blautia producta, Clostridium glycolicum, Clostridium magnum, Clostridium mayombei, Clostridium methoxybenzovorans, Oxobacter pfennigii, Thermoanaerobacter kivui, Sporomusa ovata, Thermoacetogenium phaeum, Acetobacterium carbinolicum, Sporomusa termitida, Moorella glycerini, Eubacterium aggregans, Treponema azotonutricium*, and *Terrisporobacter glycolicus*.

8. A method according to claim 1, wherein said first feedstock comprises carbohydrates, glycerol, methanol, or combinations thereof.

9. A method according to claim 1, wherein said second feedstock comprises CO, $CO_2$, carbonate, bicarbonate, $H_2$, glycerol, methanol, formate, urea or mixtures thereof.

10. A method according to claim 1, wherein said separating cells comprises filtering the fermentation broth to obtain a retentate and a permeate and recycling at least a fraction of said retentate to the fermenter.

11. A method according to claim 10, wherein said fermentation broth comprises corn water-insoluble matter and wherein said retentate comprises cells and corn water-insoluble matter at a cell to insoluble matter weight/weight ratio in a range between 10:1 and 1:10.

12. A method according to claim 1, wherein said fermentation broth further comprises at least one fermentation co-product and wherein the weight/weight ratio between said co-product and said bioproduct is in a range between 0.01 and 1.

13. A method according to claim 10, wherein said filtering comprises microfiltration.

14. A method according to claim 1, wherein said separating of the bioproduct comprises evaporating and said evaporating forms bioproduct-depleted thin stillage and wherein said thin stillage comprises an organic acid, and the method further comprises recycling said organic acid to said fermenter, wherein said organic acid is metabolized.

15. A method according to claim 1, wherein said recycling (v) comprises recycling at least 50% of said separated cells to the fermenter.

16. A method according to claim 1, wherein said separating (iv) and recycling (v) are maintained throughout fermentation.

17. A method according to claim 1, wherein the nitrogen source is selected from the group consisting of ammonium salts, yeast extract, molasses, corn water-insolubles, corn steep liquor, ethanol stillage, and combinations thereof.

18. A method according to claim 14, wherein the organic acid is acetic acid.

* * * * *

SEQUENCE LISTING

<160> NUMBER OF SEQ ID NOS: 9

<210> SEQ ID NO 1
<211> LENGTH: 1056
<212> TYPE: DNA
<213> ORGANISM: Clostridium ljungdahlii

<400> SEQUENCE: 1

```
atgaaaggtt ttgcaatgtt aggtattaac aaattaggat ggattgaaaa gaaaaaccca      60
gtgccaggtc cttatgatgc gattgtacat cctctagctg tatccccatg tacatcagat     120
atacatacgg tttttgaagg agcacttggt aatagggaaa tatgattttt aggccatgaa     180
gctgtaggtg aaatagccga agttggcagc gaagttaaag attttaaagt tggcgataga     240
gttatcgtac catgcacaac acctgactgg agatctttag aagtccaagc tggttttcag     300
cagcattcaa acggtatgct tgcaggatgg aagttttcca attttaaaga tggtgtattt     360
gcagattact ttcatgtaaa cgatgcagat atgaatcttg ccatactccc agatgaaata     420
cctttagaaa gtgcagttat gatgacagac atgatgacta ctggttttca tggagcagaa     480
cttgcagaca taaaaatggg ctccagcgtt gtagtaattg gtataggagc tgttggatta     540
atgggaatag ccggttccaa acttcgagga gcaggcagaa ttatcggtgt tggaagcaga     600
cctgtttgtg ttgaaacagc taaattttat ggagcaactg atattgtaaa ttataaaaat     660
ggtgatatag ttgaacaaat catggactta actcatggta aggtgtagaa ccgtgtaatc     720
atggcaggcg gtggtgctga acactagcaa caagcagtaa ctatggttaa acctggcggc     780
gtaatttcta acatcaacta ccatggaagc ggtgatactt taccaatacc tcgtgttcaa     840
tggggctgcg gcatggctca caaaactata agaggaggat tatgccccgg cggacgtctt     900
agaatggaaa tgctaagaga tcttgttcta tataaacgtg ttgatttgag taaacttgtt     960
actcatgtat ttgatggtgc agaaaatatt gaaaaggccc ttttgcttat gaaaaataag    1020
ccaaaagatt taattaaatc agtagttaca ttctaa                              1056
```

<210> SEQ ID NO 2
<211> LENGTH: 1179
<212> TYPE: DNA
<213> ORGANISM: Clostridium acetobutylicum

<400> SEQUENCE: 2

```
atgaaagaag ttgtaatagc tagtgcagta agaacagcga ttggatctta tggaaagtct     60
cttaaggatg taccagcagt agatttagga gctacagcta taaggaagc agttaaaaaa     120
gcaggaataa aaccgaggga tgttaatgaa gtcattttag aaatgttct tcaagcaggt     180
ttaggacaga atccagcaag acaggcatct tttaaagcag gattaccagt tgaaattcca     240
gctatgacta ttaataaggt ttgtggttca ggacttagaa cagttagctt agcagcacaa     300
attataaaag caggagatgc tgacgtaata atagcaggtg gtatggaaaa tatgtctaga     360
gctccttact tagcgaataa cgctagatgg ggatatagaa tgggaaacgc taaatttgtt     420
gatgaaatga tcactgacgg attgtgggat gcatttaatg attaccacat gggaataaca     480
gcagaaaaca tagctgagag atggaacatt tcaagagaag aacaagatga gtttgctctt     540
gcatcacaaa aaaagctga agaagctata aaatcaggtc aatttaaaga tgaaatagtt     600
cctgtagtaa ttaaaggcag aaagggagaa actgtagttg atacagatga gcaccctaga     660
tttggatcaa ctagaaagg acttgcaaaa ttaaaacctg ccttcaaaaa agatggaaca     720
gttacagctg gtaatgcatc aggattaaat gactgtgcag cagtacttgt aatcatgagt     780
```

```
gcagaaaaag ctaaagagct tggagtaaaa ccacttgcta agatagtttc ttatggttca      840
gcaggagttg acccagcaat aatgggatat ggacctttct atgcaacaaa agcagctatt      900
gaaaaagcag gttggacagt tgatgaatta gatttaatag aatcaaatga agcttttgca      960
gctcaaagtt tagcagtagc aaaagattta aaatttgata tgaataaagt aaatgtaaat     1020
ggaggagcta ttgcccttgg tcatccaatt ggagcatcag gtgcaagaat actcgttact     1080
cttgtacacg caatgcaaaa aagagatgca aaaaaaggct tagcaacttt atgtataggt     1140
ggcggacaag gaacagcaat attgctagaa aagtgctag                            1179

<210> SEQ ID NO 3
<211> LENGTH: 657
<212> TYPE: DNA
<213> ORGANISM: Clostridium acetobutylicum

<400> SEQUENCE: 3
atgaactcta aaataattag atttgaaaat ttaaggtcat tctttaaaga tgggatgaca       60
attatgattg gaggtttttt aaactgtggc actccaacca aattaattga tttttttagtt     120 aatttaaata taaagaattt aacgattata agtaatgata catgttatcc taatacaggt     180
attggtaagt taatatcaaa taatcaagta aaaaagctta ttgcttcata tataggcagc     240
aacccagata ctggcaaaaa actttttaat aatgaacttg aagtagagct ctctccccaa     300
ggaactctag tggaaagaat acgtgcaggc ggatctggct taggtggtgt actaactaaa     360
acaggtttag gaactttgat tgaaaaagga agaaaaaaa tatctataaa tggaacggaa      420
tatttgttag agctacctct tacagccgat gtagcattaa ttaaaggtag tattgtagat     480
gaggccggaa acaccttcta taaaggtact actaaaaact ttaatcccta tatggcaatg     540
gcagctaaaa ccgtaatagt tgaagctgaa aatttagtta gctgtgaaaa actagaaaag     600
gaaaaagcaa tgaccccgg agttcttata aattatatag taaaggagcc tgcataa         657

<210> SEQ ID NO 4
<211> LENGTH: 666
<212> TYPE: DNA
<213> ORGANISM: Clostridium acetobutylicum

<400> SEQUENCE: 4
atgattaatg ataaaaacct agcgaaagaa ataatagcca aaagagttgc aagagaatta       60
aaaaatggtc aacttgtaaa cttaggtgta ggtcttccta ccatggttgc agattatata     120
ccaaaaaatt tcaaaattac tttccaatca gaaaacggaa tagttggaat gggcgctagt     180
cctaaaataa atgaggcaga taaagatgta gtaaatgcag gaggagacta tacaacagta     240
cttcctgacg gcacattttt cgatagctca gtttcgtttt cactaatccg tggtggtcac     300
gtagatgtta ctgttttagg ggctctccag gtagatgaaa agggtaatat agccaattgg     360
attgttcctg gaaaaatgct ctctggtatg ggtggagcta tggatttagt aaatggagct     420
aagaaagtaa taattgcaat gagacataca aataaaggtc aacctaaaat tttaaaaaaa     480
tgtacacttc ccctcacggc aaagtctcaa gcaaatctaa ttgtaacaga acttggagta     540
attgaggtta ttaatgatgg tttacttctc actgaaatta ataaaacac aaccattgat     600 gaaataaggt ctttaactgc tgcagattta ctcatatcca atgaacttag acccatggct     660
gtttag                                                                666
```

<210> SEQ ID NO 5
<211> LENGTH: 735
<212> TYPE: DNA
<213> ORGANISM: Clostridium acetobutylicum

<400> SEQUENCE: 5

| | | | | | |
|---|---|---|---|---|---|
| atgttaaagg | atgaagtaat | taaacaaatt | agcacgccat | taacttcgcc | tgcatttcct | 60 |
| agaggaccct | ataaatttca | taatcgtgag | tattttaaca | ttgtatatcg | tacagatatg | 120 |
| gatgcacttc | gtaaagttgt | gccagagcct | ttagaaattg | atgagcccttt | agtcaggttt | 180 |
| gaaattatgg | caatgcatga | tacgagtgga | cttggttgtt | atacagaaag | cggacaggct | 240 |
| attcccgtaa | gctttaatgg | agttaaggga | gattatcttc | atatgatgta | tttagataat | 300 |
| gagcctgcaa | ttgcagtagg | aagggaatta | agtgcatatc | ctaaaaagct | cgggtatcca | 360 |
| aagcttttg | tggattcaga | tactttagta | ggaactttag | actatggaaa | acttagagtt | 420 |
| gcgacagcta | caatgggta | caaacataaa | gccttagatg | ctaatgaagc | aaaggatcaa | 480 |
| atttgtcgcc | ctaattatat | gttgaaaata | atacccaatt | atgatggaag | ccctagaata | 540 |
| tgtgagctta | taaatgcgaa | aatcacagat | gttaccgtac | atgaagcttg | gacaggacca | 600 |
| actcgactgc | agttatttga | tcacgctatg | gcgccactta | atgatttgcc | agtaaaagag | 660 |
| attgttcta | gctctcacat | tcttgcagat | ataatattgc | ctagagctga | agttatatat | 720 |
| gattatctta | agtaa | | | | | 735 |

<210> SEQ ID NO 6
<211> LENGTH: 1176
<212> TYPE: DNA
<213> ORGANISM: Clostridium kluyveri

<400> SEQUENCE: 6

| | | | | | |
|---|---|---|---|---|---|
| atgagagaag | tagttattgt | aagtgcagtg | agaacagcta | taggaagttt | cggtggaact | 60 |
| ttgaaagatg | ttccagcagt | ggaattagga | gctgtagtta | taaagaagc | agtaaaaaga | 120 |
| gcaaatgtta | agccagaaca | aatagatgaa | gttatatttg | aaacgtaat | acaggcaggt | 180 |
| cttggtcaga | gtccagcgag | acaggcagct | gtaaaagcag | gtattcctgt | agaagttcca | 240 |
| gcattcacat | taataaggt | ttgtggttca | ggacttagat | cagtaagttt | ggcagctcag | 300 |
| gttataaaag | ctggagatgc | tgatattgtc | gtagttggtg | gaatgaaaa | catgtctgct | 360 |
| gctccatatg | tactcccaaa | agctagatgg | ggacatagaa | tgggagaagg | aaaaatagtt | 420 |
| gatgctatga | taaaagacgg | actttgggag | gcattcaaca | attatcacat | gggaattaca | 480 |
| gctgaaaaca | tagcagaaaa | atggggttta | acaagagaag | agcaggatga | attttcagca | 540 |
| gcgtcccagc | aaaaagcaga | agcagctcaa | aaagcaggta | aattcaaaga | tgaaatagtt | 600 |
| ccagtaactg | ttaagataaa | aaagaaagaa | gtagttttg | atactgatga | gtatataaaa | 660 |
| ccaggaacaa | ctgttgaaac | actggcaaaa | ttgagaccag | cattcaaaaa | agatggaaca | 720 |
| gttacagcag | gtaatgcttc | aggaataaat | gatgcagcag | cagctttagt | tgtgatgagt | 780 |
| gcagataagg | caaagaaact | tggaattaaa | ccacttgcaa | agattgtttc | ctatggaagt | 840 |
| gcaggattag | atccgacaat | aatgggatat | ggtccttttc | catgcaacaa | agcagcactt | 900 |
| gaaaaagcta | acttgtcagt | tgcagattta | gacttaatag | aagcaaatga | agcattcgct | 960 |
| tcacagagtt | tggcagtagc | aaaagattta | gaatttgata | tgagcaaagt | aaatgtaaat | 1020 |
| ggaggagcaa | tagctcttgg | acatccagtt | ggagcatcag | gagcaagaat | acttgttaca | 1080 | ttacttcatg aaatgcagag aagagatgca aaaaaaggtc ttgcaacatt atgtataggc    1140 ggtggaatgg gaactgcttt aatagtagag agataa                              1176

<210> SEQ ID NO 7
<211> LENGTH: 657
<212> TYPE: DNA
<213> ORGANISM: Clostridium acetobutylicum

<400> SEQUENCE: 7
atgaactcta aaataattag atttgaaaat ttaaggtcat tctttaaaga tgggatgaca      60
attatgattg gaggtttttt aaactgtggc actccaacca aattaattga tttttttagtt   120 aatttaaata taaagaattt aacgattata agtaatgata catgttatcc taatacaggt    180
attggtaagt aatatcaaa taatcaagta aaaaagctta ttgcttcata taggcagc       240 aacccagata ctgcaaaaa actttttaat aatgaacttg aagtagagct ctctccccaa     300
ggaactctag tggaaagaat acgtgcaggc ggatctggct taggtggtgt actaactaaa    360
acaggtttag gaactttgat tgaaaaagga agaaaaaaa tatctataaa tggaacggaa     420
tatttgttag agctacctct tacagccgat gtagcattaa ttaaaggtag tattgtagat    480
gaggccggaa acaccttcta taaaggtact actaaaaact ttaatcccta tatggcaatg    540
gcagctaaaa ccgtaatagt tgaagctgaa aatttagtta gctgtgaaaa actagaaaag    600
gaaaaagcaa tgaccccggg agttcttata aattatatag taaaggagcc tgcataa      657

<210> SEQ ID NO 8
<211> LENGTH: 666
<212> TYPE: DNA
<213> ORGANISM: Clostridium acetobutylicum

<400> SEQUENCE: 8
atgattaatg ataaaaacct agcgaaagaa ataatagcca aaagagttgc aagagaatta      60
aaaaatggtc aacttgtaaa cttaggtgta ggtcttccta ccatggttgc agattatata    120
ccaaaaaatt tcaaaattac tttccaatca gaaaacggaa tagttggaat gggcgctagt    180
cctaaaataa atgaggcaga taagatgta gtaaatgcag gaggagacta tacaacagta     240
cttcctgacg gcacattttt cgatagctca gtttcgtttt cactaatccg tggtggtcac    300
gtagatgtta ctgttttagg ggctctccag gtagatgaaa agggtaatat agccaattgg    360
attgttcctg gaaaaatgct ctctggtatg ggtggagcta tggatttagt aaatggagct    420
aagaaagtaa taattgcaat gagacataca aataaaggtc aacctaaaat tttaaaaaaa    480
tgtacacttc ccctcacggc aaagtctcaa gcaaatctaa ttgtaacaga acttggagta    540
attgaggtta ttaatgatgg tttacttctc actgaaatta ataaaaacac aaccattgat    600
gaaataaggt ctttaactgc tgcagattta ctcatatcca atgaacttag acccatggct    660
gtttag                                                              666

<210> SEQ ID NO 9
<211> LENGTH: 735
<212> TYPE: DNA
<213> ORGANISM: Clostridium acetobutylicum

<400> SEQUENCE: 9
atgttaaagg atgaagtaat taaacaaatt agcacgccat taacttcgcc tgcatttcct     60
agaggaccct ataatttca atcgtgag attttaaca ttgtatatcg tacagatatg       120
gatgcacttc gtaaagttgt gccagagcct ttagaaattg atgagcccct agtcaggttt    180

```
gaaattatgg caatgcatga tacgagtgga cttggttgtt atacagaaag cggacaggct    240
attcccgtaa gctttaatgg agttaaggga gattatcttc atatgatgta tttagataat    300
gagcctgcaa ttgcagtagg aagggaatta agtgcatatc ctaaaaagct cgggtatcca    360
aagctttttg tggattcaga tactttagta ggaactttag actatggaaa acttagagtt    420
gcgacagcta caatgggta caaacataaa gccttagatg ctaatgaagc aaaggatcaa    480
atttgtcgcc ctaattatat gttgaaaata atacccaatt atgatggaag ccctagaata    540
tgtgagctta taaatgcgaa aatcacagat gttaccgtac atgaagcttg gacaggacca    600
actcgactgc agttatttga tcacgctatg gcgccactta atgatttgcc agtaaaagag    660
attgtttcta gctctcacat tcttgcagat ataatattgc ctagagctga agttatatat    720
gattatctta agtaa                                                    735
```